(12) United States Patent
Baldwin et al.

(10) Patent No.: US 7,368,289 B2
(45) Date of Patent: May 6, 2008

(54) FILTER FOR DETERMINATION OF MERCURY IN EXHAUST GASES

(75) Inventors: Tom Baldwin, Reno, NV (US); John Ward, III, Reno, NV (US); Allan Budd, Sun City, AZ (US)

(73) Assignee: Perma Pure LLC, Boonton, NJ (US)

( * ) Notice: Subject to any disclaimer, the term of this patent is extended or adjusted under 35 U.S.C. 154(b) by 755 days.

(21) Appl. No.: 10/703,112

(22) Filed: Nov. 7, 2003

(65) Prior Publication Data

US 2005/0084976 A1   Apr. 21, 2005

Related U.S. Application Data

(60) Provisional application No. 60/512,093, filed on Oct. 20, 2003.

(51) Int. Cl.
*G01N 33/00*   (2006.01)

(52) U.S. Cl. .............................. 436/81; 422/83; 422/86; 422/88; 422/99

(58) Field of Classification Search .................. 422/83, 422/86, 88, 99; 436/81
See application file for complete search history.

(56) References Cited

U.S. PATENT DOCUMENTS

| | | | |
|---|---|---|---|
| 4,161,883 A | 7/1979 | Laird et al. | |
| 5,807,750 A * | 9/1998 | Baum et al. | ................. 436/164 |
| 5,879,948 A * | 3/1999 | Van Pelt et al. | ............... 436/81 |
| 6,200,816 B1 | 3/2001 | Farber et al. | |
| 6,475,802 B2 | 11/2002 | Schaedlich et al. | |
| 6,736,883 B2 | 5/2004 | Sjostrom et al. | |
| 7,144,736 B2 * | 12/2006 | Noda et al. | .................... 436/81 |

OTHER PUBLICATIONS

Declaration of inventor Thomas Baldwin regarding experimental use transaction for first prototype not previously used or tested, dated Oct. 17, 2004.
Liu, Kunlei, et al. "Application of PS Analytical Continuous Mercury Monitor to Utility Unit." Air Quality IV, Sep. 22-24, 2003.
Kilgroe, James. "Fundamental Science and Engineering of Mercury Control in Coal-Fired Power Plants."
Chu, Paul, et al. "'Longer-Term' Mercury Emissions Variability from Coal-Fired Power Plants."
Sjostrom, Sharon, et al. "Performance Evaluation of Inertial Separation Probes for Vapor-Phase Mercury Measurements."
"Heated Stack Filter Head Assembly Series 30 and 40 Instruction Manual." Probe Manual 30-40 Series, Nov. 14, 1997.

* cited by examiner

*Primary Examiner*—Jill Warden
*Assistant Examiner*—Samuel P Siefke
(74) *Attorney, Agent, or Firm*—Dinsmore & Shohl LLP

(57) ABSTRACT

An apparatus, process, coating, and filter for the accurate measurement of total mercury concentration in flue gas. In a preferred aspect, the concentrations of both elemental and oxidized mercury are preserved by the apparatus for analysis. Accordingly, embodiments of the present apparatus and process can be used to determine regulatory compliance or for process control measurement.

12 Claims, 7 Drawing Sheets

FILTER FOR DETERMINATION OF MERCURY IN EXHAUST GASES

This application claims the benefit of U.S. Provisional Patent Application Ser. No. 60/512,093 filed Oct. 20, 2003, the contents of which are hereby incorporated by reference in their entirety.

FIELD OF THE INVENTION

The present inventive subject matter relates generally to an apparatus, process, coating, and filter for accurately measuring total gaseous mercury concentration in flue gas. In one aspect, the preferred embodiments preserve the true concentrations of both elemental and oxidized mercury in flue gas for analysis. Accordingly, the preferred embodiments can be used to determine regulatory compliance or for process control measurement.

BACKGROUND OF THE INVENTION

Mercury (Hg) has been designated a toxic compound found in the environment by the EPA. The Draft EPA Mercury Study Report to Congress estimates total annual mercury emissions from anthropogenic sources globally is 4,000 tons, with 200-300 metric tons emitted annually in the U.S. The report identifies the largest sources of mercury emissions in the U.S. to be utility boilers, followed by waste incinerators which combust mercury-containing wastes (municipal and medical), coal-fired industrial boilers, and cement kilns that combust coal-based fuels. Other potentially important sources of mercury emissions are manufacturing plants and basic chemical processes. One particularly notable source of mercury emissions is coal-fired power plants. These plants emit 48 tons of mercury per year, and will be required to reduce this emission level by greater than 90% by 2010.

The EPA published regulatory guidelines for mercury emissions from municipal waste combustors in 1995. To quantify the emissions from each point source, a mercury CEMS (Continuous Emissions Monitoring System) will be required. There are three forms of mercury in smoke stack effluent gas, or flue gas, from a coal fired power plant that can potentially be monitored by a mercury CEMS, namely elemental $Hg^0$, oxidized $Hg^{+2}$, and particulate bound Hg of either species, at stack gas temperatures in excess of 200° F. However, the EPA does not currently require the continuous monitoring of particulate bound $Hg^0$. Accordingly, total mercury continuously monitored in accordance with EPA regulations, i.e., gaseous mercury, is the sum of elemental mercury ($Hg^0$) and oxidized mercury ($Hg^{++}$). However, Massachusetts and Wisconsin plan to regulate particulate bound $Hg^0$ starting in the year 2006.

Mercury in both of these gaseous forms is very sticky chemically, having a strong affinity to adsorb onto a wide variety of surfaces, and extremely difficult to handle and transport through an extractive gas sampling system to a gas analyzer for measurement. Since flue gases usually contain very low levels of gaseous mercury that must be detected, the small amount present that readily adsorbs onto surfaces of tubing, valves, and other fittings distorts any reading made.

Further, the more restrictive controls on air toxic mercury mandated by the EPA will likely result in higher operational costs to flue gas generators, such as coal-fired plant owners. Accordingly, there exists a real and eminent need for the development of a durable, low cost, accurate technology capable of measuring mercury species and total mercury emitted in a smoke stack effluent gas in real-time. A total mercury measurement is required for regulatory monitoring, whereas the evaluation of mercury control technologies and manufacturing processes requires measurements that reveal the distribution of elemental and oxidized mercury.

Various approaches in the development of CEMS's for mercury measurement in flue gas emissions to determine the amount of elemental or reduced mercury ($Hg^0$) therein have included x-ray diffraction, UV photometry, cold vapor Atomic Absorption, and atomic fluorescence methods. Some methods detect and measure amounts of elemental or reduced mercury at excitation wave lengths of 254 nm. Unfortunately, any oxidized species of mercury ($Hg^{++}$) therein cannot likewise be measured.

In order to measure total mercury, the oxidized mercury species state ($Hg^{++}$) must first be reduced to $Hg^0$. The predominant form of oxidized mercury existing in flue gas coal fired combustors, waste combustors, and incinerators is $HgCl_2$ (C. S. Krivanek, III, Journal of Hazardous Materials, 47 (1996) *Mercury Control Technologies for MWC's: The Unanswered Questions*, pp. 119-136 and IEA Coal Research, *Mercury Emissions and Effects—The Role of Coal*). It is presently known that by measuring the elemental mercury concentration in a gaseous matrix both prior and subsequent to a mercury reduction process, the total mercury concentration and the distribution of oxidized and reduced mercury can be determined. The determination of this distribution is of significant value, and often essential, in the development of effective mercury control options for gaseous emissions and can have value to effective process quality control.

Typically, in order to measure the total mercury concentration of a sample by laboratory analysis, the reduction of oxidized mercury involves the mixing of a gas or liquid sample with reducing solutions prior to measurement of $Hg^0$. Similarly, several instrument manufacturers have incorporated reducing solutions into their on-line CEMS's for mercury measurement in the exhaust gasses of flue stacks. These devices rely on reducing solutions such as sodium hydroboride solution, stannous chloride solution, or other reducing solutions to convert oxidized mercury to $Hg^0$ prior to measurement by a detector such as an ultraviolet (UV) atomic absorption (AA) or atomic fluorescence detector. An obvious disadvantage to this type of instrument design is that it requires frequent solution replenishment.

Further, a dry mercury reduction method is preferable to a wet one in continuous on-line measurement since there are fewer maintenance requirements, which, in turn, translates to a more reliable technique. Thermal reduction of oxidized mercury is such an alternative dry method; it is reported in the open literature that oxidized mercury can easily be reduced at temperatures of about 800° C. However, a gaseous exhaust from a coal-fired boiler or incinerator may often contain oxidizing agents that can and will reoxidize the thermally reduced mercury before a mercury measurement can be effected.

For example, the fossil-fueled and waste combustion industries generate gaseous mixtures which typically contain compounds such as $NO_x$, $O_2$, $H_2O$, $CO_2$, and CO. Other gases such as $SO_2$, HCl, $Cl_2$, $H_2S$, $NH_3$, and volatile metals and organics also may be present depending on the type of fuel combusted. Of these components, hydrochloride gas and oxygen typically have a noticeable effect on the reoxidation of elemental mercury. Furthermore, the presence of oxygen in admixture with HCl gas acts to enhance the hydrochloride effect on elemental mercury oxidation.

The effect of hydrochloride on the reoxidation of elemental mercury upon thermal reduction is also reported by Wang et al., "Water, Air and Soil Pollution" 80: 1217-1226, 1995. Wang et al. used crushed quartz chips to fill a quartz cell and thereafter heated their cell to 850°-900° C. to reduce $Hg^{++}$ in a gaseous stream. They also found the addition of HCl to the gaseous matrix negated the converter effect. Their approach to counter the HCl effect was to fill the converter with basic materials. Filling the quartz converter cell with a layer of soda lime, sodium carbonate, or crushed quartz treated with NaOH solution improved the overall conversion efficiency by reacting the basic materials filling the conversion tube with hydrochloride (HCl) gas and preventing the reoxidation of elemental mercury.

The effectiveness of these approaches was limited, however, due to the severe corrosive nature of the basic solids. Further, the high temperatures necessary for the conversion that Wang et al. reported destroyed their converter cells within two days. To solve these problems, the use of an inertial filter to separate mercury vapor species from the particulate in a stack gas stream has been proposed.

There are numerous prior art inertial filter systems known for use in processing extractive gas sample conditioning systems. The inertial filter itself is an invention of the Bendix Corporation (U.S. Pat. No. 4,161,883) based on work done by Carl Laird. Mott Metallurgical Corporation has since offered an entire line of inertial filters for various applications. Accordingly, these inertial bypass filters have been used in the art for many years. The construction of these prior inertial filters is a porous tube within a solid tube with a very small annular space in between the two tubes.

The basic principle of operation of the inertial filter is to accelerate the particulate material contained in the process gas in a vector direction with sufficient velocity to prevent the particles from sticking to the walls of the sampling tube. This enables the extraction, at a 90° angle, of a small aliquot sample at very low face velocity, for transportation to a gas analyzer. The basic principle is to provide a 70-100 fps (feet per second) gas velocity down the center of the porous tube at a flowrate sufficient to prevent the majority of the particulate matter from adhering to the porous tube and without penetration through the porous tube. The flow rate is dependent upon the gas density, temperature, diameter of the sampling tubing, absolute pressure, and particulate loading.

Particles subjected to a velocity of 70-100 fps continue to travel in the straight vector direction, and the sample aliquot is withdrawn axially, at a very low filter face velocity of 0.005 fps, separating the sample aliquot from the initial particulate material. The center bore tubing is typically made from sintered stainless steel, available in various micron sizes, made to order. The micron size chosen for this application is usually about 0.5 microns.

It is generally known that these prior art inertial bypass filters are heated to prevent condensation of the analyte. It is further known that either direct or indirect heating can be used in this regard. Current state of the art sample acquisition systems, then, rely on heated filters to extract flue gas from the flowing process, remove particulate material, and transport the clean sample to the sample conditioning system for analysis.

U.S. Pat. No. 6,475,802 attempted to combine this concept of using an inertial filter with the use of quartz chips taught by Wang et al. to prepare an improved process for measuring and detecting total gaseous mercury concentration in flue gases. This patent teaches a module for detection of amounts of gaseous mercury in both ambient air and flue gases. The module uses packed quartz chips to adsorb elemental and oxidized gaseous mercury to prevent their removal from a flue gas stream upon passage through a filter to remove unmeasurable particulates. Accordingly, this patent requires a denuder to strip the gaseous mercury components from a gas sample before the sample is passed through a filter to remove the particulates.

The inertial bypass filter apparatuses presently known in the art for continuously measuring quantities of mercury in smoke stack effluent gas further have the disadvantage of having to maintain a fairly constant temperature at about 200° C. to provide anything resembling an accurate measurement. However, these prior art apparatuses are unable to make a very precise measurement of the amount of mercury in the flue gas.

Additionally, these prior art apparatuses alter the flue gas in order to take an adequate measurement of the amount of mercury contained therein. Accordingly, these gases do not output the prior art apparatuses in the same state in which they entered the apparatuses. However, the mercury removal processes generally employed by the facility operator will require that the concentrations of elemental and oxidized mercury species be preserved by the sampling system for analysis, i.e., the flue gas cannot be altered. In other words, to achieve good analytical results, the filtering process at the sample point should not change the species of mercury existing in the sample and should not attenuate (adsorb) the mercury.

Another disadvantage is that these prior art filters coat up with particulate material, attenuating the mercury concentrations transported across the filter. Blowback is employed to periodically remove the particulate coating on the filter, by back purging dry, compressed air under high pressure (100 psig). However, $Hg^0$ is oxidized to $Hg^{+2}$ across the filter media, caused in part by reaction with artifacts in the particulate matter coating on the filter media as well as reaction with the filter media itself.

Accordingly, typically it has been difficult to use known apparatuses to sample total mercury concentration in flue gas without altering the ratios of oxidized to elemental mercury and without attenuating the concentrations of either species. A standard inertial filter typically will not yield good results when sampling mercury species in flue gas. Due to its chemical nature, $Hg^0$ and $Hg^{+2}$ are difficult to transport across a filter media. Typically, the filter media must be held at a temperature of 400° F. or better, and the filter media isolated from the mercury species to prevent oxidation of elemental Hg and to avoid reduction of oxidized Hg to elemental.

BRIEF SUMMARY OF ASPECTS OF THE INVENTION

The present inventive subject matter relates generally to a process, apparatus, coating, and filter for the measurement of total gaseous mercury concentration in flue gas. In one preferred aspect, the present processes and apparatuses are capable of improving the accuracy of the total gaseous mercury measurement required by the EPA by minimizing the loss of oxidized mercury through adsorption (and absorption) of the gaseous mercury in the gas sample on the particulate removal filter and other metal surfaces in the apparatus used for sampling mercury. In addition, preferred processes and apparatuses also enable the measurement of the individual concentrations of elemental mercury and oxidized mercury by preventing the catalyzed oxidation of elemental mercury on metal surfaces of the apparatus including the filter, and preferably also other metal surfaces, at the desired operating temperature of the sampling system.

Preferably, the present subject matter addresses one of the many sample-conditioning components necessary to transport gaseous mercury in both forms ($Hg^0$ and $Hg^{+2}$) to the gas analyzer. Preferred aspects relate to sample acquisition; the first components to contact the extracted process gas; the stinger (sampling probe inserted into the process gas); and the sample gas filtering system used to separate the particulate material found in the process gas from the $Hg^0$ and $Hg^{+2}$ vapor species to be analyzed.

These preferred aspects are achieved herein by rendering passive metallic surfaces of a sintered metal filter media used in an inertial filter to prevent any catalysis or deposition of gaseous mercury thereon during analyte transport through the filter. This is preferably achieved by spherically coating each individual metallic particle in the sintered metal filter media.

A preferred embodiment relates to a process for accurately measuring total gaseous mercury concentration in flue gas comprising the steps of:
(1) removing a gas sample from flue gas containing gaseous mercury using a gas sample acquisition probe;
(2) passing the gas sample through a porous filter element in an inertial filter to remove particulate material present in the gas sample; and
(3) measuring the amount of gaseous mercury present in the gas sample.

In this embodiment, all metal surfaces of the inertial filter are coated with a protective coating to prevent chemical reactions between the metal surfaces and the gas sample.

Another preferred embodiment relates to an apparatus for collecting a gas sample of flue gas containing gaseous mercury and accurately measuring the total gaseous mercury concentration therein comprising:
(1) a gas sample acquisition probe mounted into the flue gas;
(2) a porous filter element inside an inertial filter that removes particulate material from the gas sample and outputs a particulate free gas sample;
(3) an analyzer for measuring the amount of gaseous mercury present in the particulate free gas sample; and
(4) sample transport tubing used to transport the gas sample from the probe to the inertial filter, and the particulate free gas sample from the inertial filter to the analyzer.

In this embodiment, each of the probe, inertial filter, and sample transport tubing contain metal surfaces that come into contact with the gas sample or the flue gas. The metal surfaces of this inertial filter are in turn coated with a protective coating that reduces chemical reactivity to the gaseous mercury, but does not impede gas flow through the inertial filter.

Yet another preferred embodiment relates to a protective coating on metal surfaces of a gas sample acquisition and filtration apparatus for collecting a gas sample of flue gas containing gaseous mercury and removing particulate material therefrom. This protective coating reduces chemical reactivity on the metal surfaces to the gaseous mercury, but does not impede gas flow through the apparatus. In this regard, the coating is on all metal surfaces of the apparatus coming into contact with the gas sample or the flue gas.

Still another preferred embodiment relates to an inertial filter for removing particulate material from a gas sample of flue gas containing gaseous mercury without removing or chemically altering the gaseous mercury. The inertial filter comprises a stainless steel housing having a metal surface and a porous filter element having a metal surface to remove the particulate material from the gas sample. All metal surfaces of the inertial filter coming into contact with the gas sample are coated with a protective coating that reduces their chemical reactivity to the gaseous mercury, but does not impede gas flow through the inertial filter.

It is to be understood that a given embodiment need not meet all aspects or provide all the disparate features noted above. On the contrary, the scope of the invention is measured by the claims as issued and not by this brief summary of aspects of the invention.

BRIEF DESCRIPTION OF THE DRAWINGS

The preferred embodiments are disclosed in connection with the attached Figures in which.

DETAILED DESCRIPTION OF THE PREFERRED EMBODIMENTS

Definitions

Figure 1:
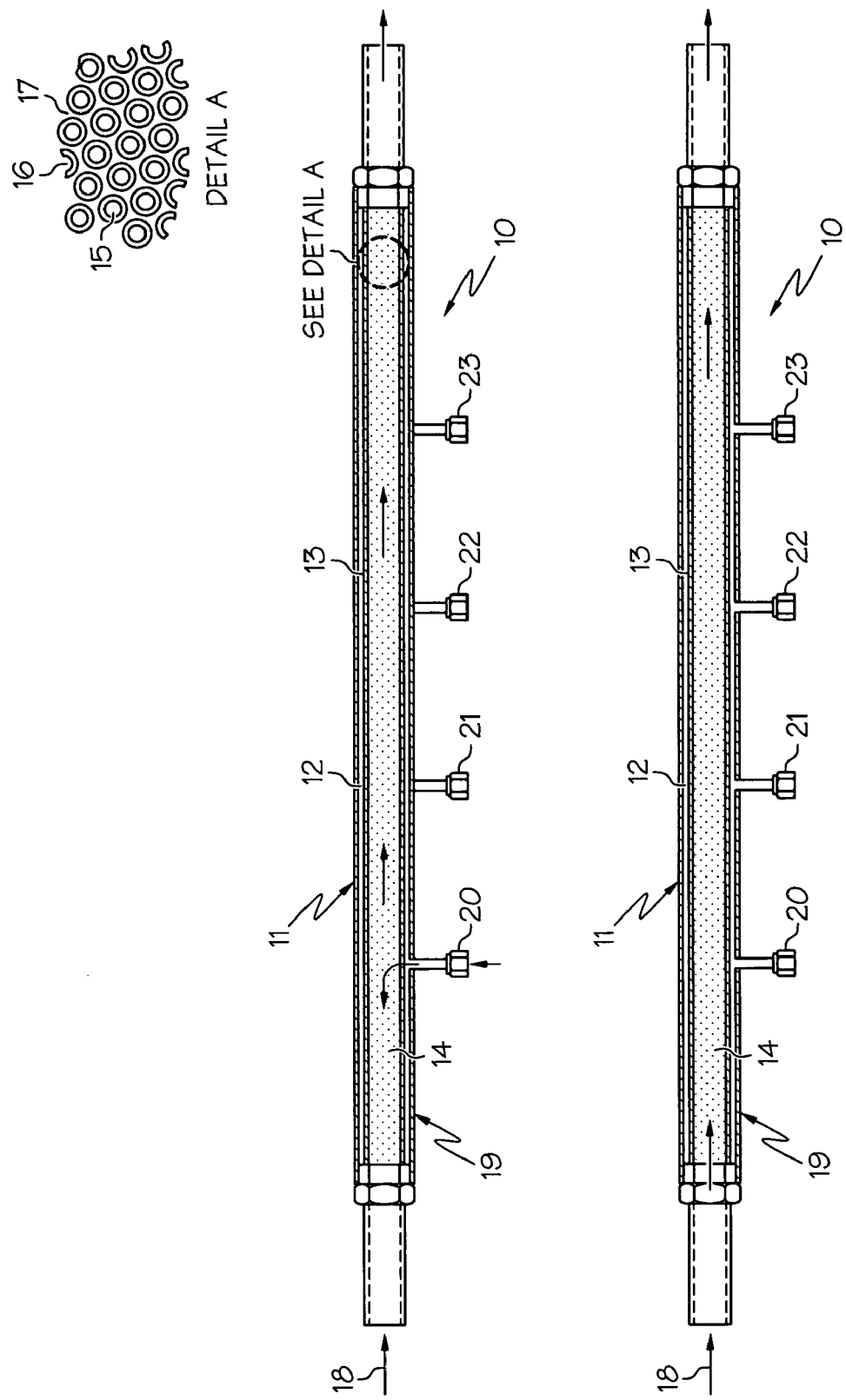
FIG. 1 is a filter flow diagram of the present inertial filter apparatus. Included is an exploded view showing that the surfaces coming in contact with the gas sample are coated with fused silica.

As used herein, the terms "elemental mercury", "elemental Hg", "metallic mercury," "reduced mercury", "non-ionized mercury vapor", "Hg(0)", and "$Hg^0$" all mean and refer to the same form of mercury.

As used herein, the terms "oxidized mercury", "oxidized Hg", "reactive gaseous mercury", "ionic mercury", "Hg(II)", "$Hg^{++}$", and "$Hg^{+2}$" all mean and refer to the same form of mercury.

As used herein, "gas sample" means a portion of gas removed from flue gas flowing anywhere in a combustor's process by the preferred apparatus. Once removed from the flue gas, particulates are removed from the gas sample, which is then analyzed and measured to determine total gaseous mercury concentration therein, corresponding to the total gaseous mercury concentration of the flue gas.

A preferred apparatus may contain the parts of a Sample Acquisition or Gas Sampler, Sample Transport, Sample Conditioning, and Flow Control/Gas Manifold to provide clean, particulate free, wet or dry flue gas samples for analysis by a gas analyzer and data recorder.

As used herein, "sample acquisition" refers to the active removal of a gas sample from flue gas flowing anywhere in a combustor's process. The "sample acquisition", "gas sample acquisition probe", or "gas sampler" portion of the apparatus is typically a removable probe (stinger) mounted into the flowing gas process.

As used herein, "sample transport" refers to those portions of the preferred apparatus that transport, or convey, a gas sample throughout the apparatus. Typically, sample transport is conducted through the use of tubing.

As used herein, "analyzer" or "gas analyzer" refers to a piece of equipment known in the art as capable of measuring total gaseous mercury concentration in a gas sample.

As used herein, "sample conditioning" refers to the removal of particulates from the gas sample, permitting measurement of the concentration of total gaseous mercury in the gas sample by the gas analyzer. Preferably, the "sample conditioning" portion of the apparatus comprises an internal or external filter assembly for immediate removal of particulate material. Accordingly, a preferred apparatus uses an inertial filtering system for sample conditioning.

Inertial Filter

The preferred apparatus contains an inertial filter to remove particulates from the flue gas sample before measurement for total gaseous mercury concentration. The inertial filter is capable of removing the particulate material in the flue gas sample, yet permits the passage of both forms of gaseous mercury in chemically unaltered form for subsequent analysis. The inertial filter, and the apparatus as a whole, does not oxidize elemental mercury or reduce oxidized mercury, so that a user may determine how much mercury in the flue gas is in each state.

Generally, inertial filters are constructed as a porous tube within a solid tube with a very small annular space in between the two tubes. The basic principle of operation of the inertial filter is to accelerate the particulate material contained in the gas sample in a vector direction with sufficient velocity to prevent the particles from sticking to the walls of the sampling tube. This enables the extraction, at a 90° angle, of a particulate-free gas sample, at very low face velocity, for transportation to a gas analyzer. The basic principle is to provide a 70-100 fps (feet per second) gas velocity down the center of the porous tube at a flowrate sufficient to prevent the majority of the particulate matter from adhering to the porous tube and without penetration through the porous tube. The flow rate is dependent upon the gas density, temperature, diameter of the sampling tubing, absolute pressure, and particulate loading. The ratio of straight vector particle velocity to the radial (axial) gas sample velocity should be greater than 10,000:1. In a preferred embodiment, the ratio is about 14,000:1 (i.e., about 70 fps/0.005 fps).

Particles subjected to a velocity of 70-100 fps continue to travel in the straight vector direction, and the gas sample is withdrawn at a very low filter face velocity of 0.005 fps, separating the gas sample from the initial particulate material. The center bore tubing, or porous filter element, is preferably made from a sintered metal filter media, available in various micron sizes, made to order to remove particulate material from the gas sample. The micron size chosen for this application is usually from about 50 to about 0.1 microns. In a preferred embodiment the final micron size of the inertial filter used in the present apparatus is about 0.5 microns. In a particularly preferred embodiment, the sintered metal filter media is sintered stainless steel. Further, the porous filter element may have an inner diameter of between approximately ¼" and ½", preferably approximately ¼", ⅜", or ½", and a length of approximately 12 to approximately 24 inches.

Stainless steel or other metals are desirable as the material of construction for the housing, or solid tube, of the inertial filter and associated structure that transports the gas sample to the analysis system due to its mechanical ruggedness and ability to withstand the high temperatures that are necessary to prevent condensation. Stainless steel, however, typically catalyzes the oxidation of elemental mercury to oxidized mercury. It also has a propensity to adsorb and desorb oxidized mercury. Other materials such as glass, quartz, or Teflon® will not do either of these and would be much better than untreated stainless steel, although with these materials problems can arise such as brittleness in the case of glass and quartz and mechanical instability in the case of Teflon® and other plastics.

In an alternative preferred embodiment, the inertial filter can be made up of a ceramic rather than a metal such as stainless steel. While not as durable as stainless steel, a ceramic filter avoids the problems of catalyzing the oxidation of elemental mercury to oxidized mercury and adsorption and desorption of oxidized mercury. Accordingly, a ceramic inertial filter does not require a treatment or coating as does a stainless steel inertial filter described herein to still be effective in transporting gaseous mercury.

Protective Coating

The preferred inertial filters solve these difficulties by incorporating a protective coating on all metal surfaces coming in contact with the gas sample. The protective coating can be coated on the metal surfaces by processes well known to those of ordinary skill in the art. In preferred embodiments, the metal surfaces coated with the protective coating are comprised of stainless steel. This coating stops the catalysis of mercury oxidation and drastically reduces the adsorption of oxidized mercury.

In a preferred embodiment, the non-metallic coating can be comprised of any material capable of coating the individual metallic particles of the inertial filter, which is stable at an operating temperature of 450° F. or less, and which produces a finished filter porosity of 0.1 microns or greater. Specific examples of materials useful in forming the protective coating on the metal surfaces coming in contact with the gas sample are those selected from the group consisting of fused silica (a form of quartz), a fused silica derivative, a fused silica-like material, silica-oxide, Teflon®, Viton, Silicone, Silcosteel®, Deactivated Fused Silica Lined®, Silane Deactivated Fused Silica, Silane, Sulfinert™, Siltek®, Passivation, Passivation Coatings, Quartz, Glass, Ceramic, Plastic, Restek®, Titanium, Titanium Derivative, Polymer, Copolymer, Magnesium, Magnaplate, Nedox®, Urethane, Buna, Kalrez®, Chemraz®, Aegis, Neoprene, Flouro Silicone, Elastomer, Latex, Rubber, Isoprene, Butadiene, Styrene, Butyl, Ethylene, Propylene, Nitrile, Epichlorohydrin, Hypalon, Polysulfide, Silicone Polymer, Fluorocarbon Polymer, Acrylic Ester, Acrylic Halide, and combinations thereof. In a particularly preferred embodiment, the protective coating on the metal surfaces is comprised of a thin layer of fused silica or a derivative thereof.

In particular, silica and its derivatives are among the few materials capable of putting a coating with a thickness of up to approximately several thousand Angstroms (a few molecules thick) on the metal surfaces of the inertial filter in order to prevent gas sample contact with the surface but not impede gas sample flow through the filter. Accordingly, in a preferred embodiment the coated inertial filter will have a filter porosity of about 0.5 microns. The present preferred apparatus, then, is capable of measuring the individual concentrations of elemental mercury and oxidized mercury in a flue gas sample by preventing the catalyzed oxidation of elemental mercury on the metal surfaces of the apparatus, such as the porous filter element, at the desired operating temperature of the sampling system.

The protective coating isolates the gaseous mercury species, both $Hg^0$ and $Hg^{+2}$, from the porous filter element and transports the $Hg^0$ and $Hg^{+2}$ vapor without any loss across the filter, retaining the $Hg^0$ to $Hg^{+2}$ concentration ratio existing in the flue gas. Accordingly, the protective coating prevents chemical or physical alteration of the gas sample passing through the inertial filter. This permits the accurate measurement of the $Hg^{+2}$ and/or the $Hg^0$ gaseous mercury species.

The protective coating serves to reduce chemical reactivity of the metal surfaces coming in contact with the gaseous mercury to said gaseous mercury, without impeding gas flow through the inertial filter. Such chemical reactions reduced on the metal surfaces include, without limitation, oxidation of elemental mercury to a chemically combined form of mercury and loss of oxidized mercury through adsorption on the metal surfaces.

As it passes over quartz or other non-catalytic surfaces, the oxidation of elemental mercury to oxidized mercury, aided by the presence of chloride radical ($Cl^-$), takes place at a much higher temperature than it does when passed over a metal surface, such as those materials that make up stainless steel. By coating the surface of the metal parts of the sampling system with for example, fused silica or its derivatives, the preferred apparatus prevents the mercury from contacting the metal surface where its oxidation will be "catalyzed" by the metal. Thus, the state of the mercury in the sample is preserved for subsequent analysis.

Further, elemental mercury has a tendency to be adsorbed by certain metal surfaces, i.e., attach itself to these metal surfaces such as stainless steel. Accordingly, by coating the metal surfaces of the preferred apparatus with a film of, for example, fused silica or derivatives thereof, the elemental mercury will bead up and quickly leave the surface since it cannot adsorb to the metal surface. Mercury is repelled by the fused silica or derivative thereof, rather than attracted to the metal surface, and can pass by the metal, remaining in the gas phase for subsequent analysis.

These two phenomena are related in that, in most catalytic processes, the intimate contact of the material with the catalyst is necessary and adsorption is often involved in catalytic processes. The fused silica or fused silica derivative coating is a barrier that prevents either form of mercury from getting in contact with the metal surface.

The porous filter element of the preferred apparatus, if comprised of a metal rather than a ceramic, must bear this protective coating, such as a coating of fused silica or a derivative thereof, because it has the highest surface area. However, particularly preferred embodiments further contemplate that all metal surfaces of the apparatus that come into contact with, or are wetted by, the flue gas sample, or the flue gas itself, are coated with a protective coating that reduces chemical reactivity of all of these metal surfaces to gaseous mercury. Accordingly, components of the apparatus that may bear such a coating may include but are not limited to the following:

1. stinger (sampling probe inserted into the stack, duct, or pipe);
2. sintered metal filter media used for primary particulate separation;
3. sample transport stainless steel tubing;
4. tube fittings used for sample tubing interconnections;
5. gas sampling pump for transporting the sample under pressure;
6. flow control valves for controlling flow;
7. heated stainless steel transport bundle for transporting the sample gas to the sample conditioning system;
8. stainless steel impingers within a thermo electric or refrigeration sample cooler; and
9. solenoid gas control valves.

Accordingly, the protective coating enables the preferred apparatuses and processes to provide near real time, on-line monitoring of metal emissions and chemical emissions in flue gases and for archiving of the sample results. The preferred apparatus and process, then, can be used to monitor flue gases from a number of entities, including, but not limited to, furnaces, incinerators, smelters, iron and steel plants, lime and cement kilns, battery plants, and semiconductor plants. An exemplary application is the analysis of fly-ash from coal combustion.

Processes of Preparing Protective Coating

A preferred process for coating the apparatus with, for example, fused silica or a derivative thereof bonds a layer of fused silica or a fused silica derivative to the sintered metal filter media, and all other metal surfaces coming into contact with the gas sample during sample transport. This process bonds thin, uniform, flexible layers (up to several thousand angstroms) of fused silica or its derivatives to the surface of the metal surfaces in the preferred apparatus. The fused silica coating is as inert as Teflon® or a glass composite filter media, and it can be used to transport gaseous mercury without chemically altering it at operating temperatures exceeding 400° F.

For example, a preferred process for coating the sintered metal filter media would start out with a sintered filter of large pore size, such as about 50 microns. Layers of the fused silica coating are then progressively applied to the sintered filter. After the coating is completed, the coated sintered metal filter media should preferably have an about 0.5 micron pore size. This coating process is preferably conducted using a gas phase coating process in order to permit the spherical coating of each individual filter particle, rendering each particle benign.

Passivation of the fused silica layer can be improved further by adding a secondary chemical deactivation layer. The purpose of the chemical deactivation layer is to cover any silanol (—Si—OH) groups on the surface of the coating of fused silica or a derivative thereof. The standard deactivation chemical used by industry is an intermediate polarity siloxane containing phenyl and methyl moieties. Silanol is normally not a problem when transporting mercury through the porous filter element, but under certain applications, a secondary coating on the fused silica is necessary.

In another preferred embodiment, all metal surfaces of the apparatus coming in contact with the flue gas are similarly coated with a polymer coating. In this embodiment, thin, uniform, flexible layers (up to several thousand angstroms) of the polymer are bonded to the sintered metal filter media, and all other metal surfaces coming into contact with the gas sample during sample transport. The polymer coating can be used to transport gaseous mercury without chemically altering it at operating temperatures below 400° F. The polymer coating is preferably applied using a gas phase coating process in order to permit the spherical coating of each individual filter particle, rendering each particle benign.

Preferred Apparatus Components

A filter flow diagram of a particulate laden stream 18 through the preferred inertial filter 10 is shown in FIG. 1. The inertial filter 10 comprises an outer filter housing 11 made up of a housing annulus 12 and a porous wall 13. Inside the filter housing 11 is a porous filter element 14 having a fused silica coating 15 of molecular thickness surrounding the filter particles 16, leaving interstitial spaces 17 of approximately 0.5 microns each between each coated filter particle. A particulate laden stream 18 enters the inertial filter 10 and travels in the filter air flow direction 19. Also present are a blowback air inlet 20, a calibration gas input 21, a sample output 22, and a filter surface temperature thermocouple 23.

Figure 2:
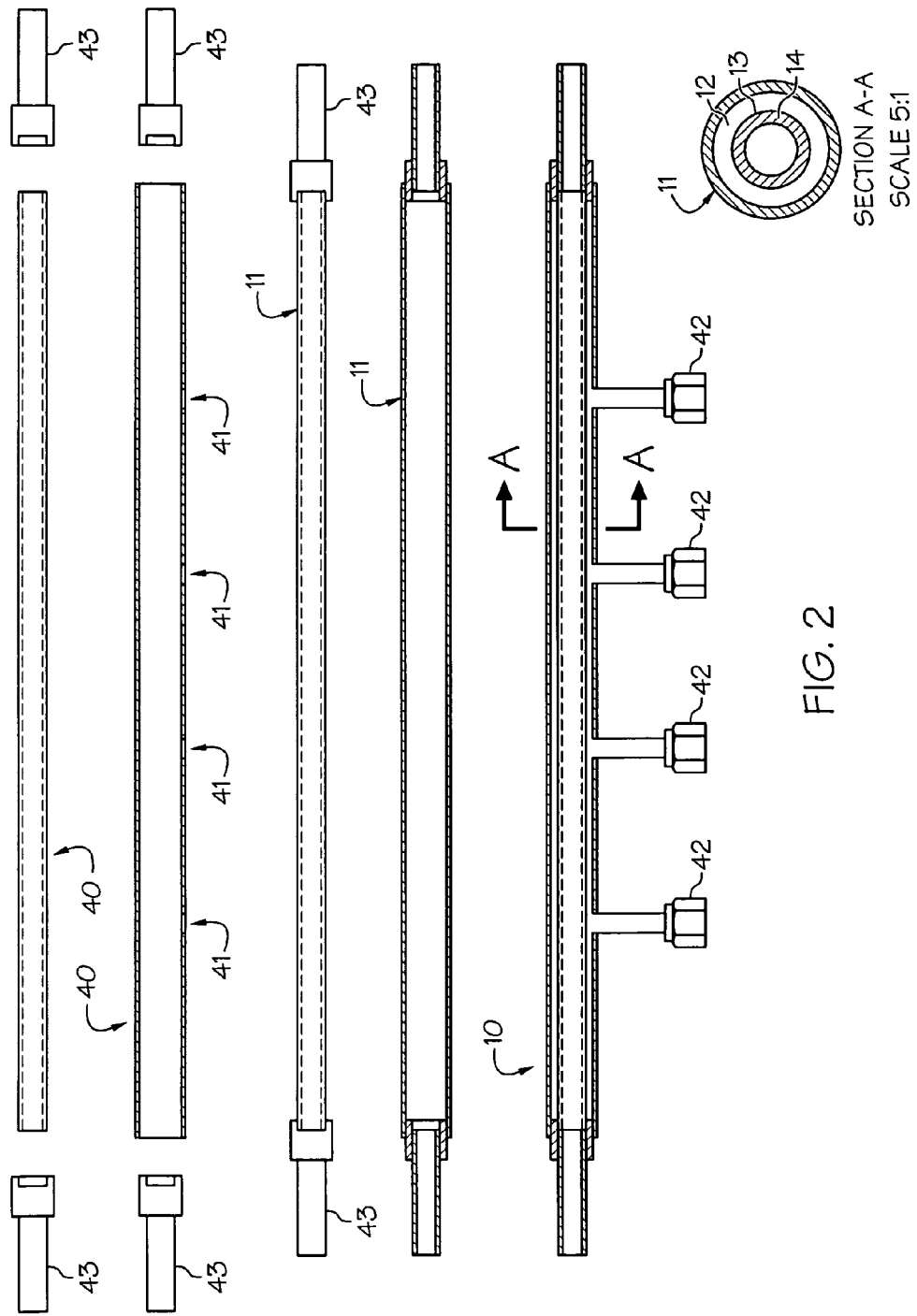
FIG. 2 is a diagram of the present inertial filter apparatus, including a cross sectional drawing thereof.

Another schematic depiction, as well as a cross-sectional view, of the preferred inertial filter is shown in FIG. 2 as numeral 10. The outer filter housing 11 of the inertial filter 10 is made from a stainless steel pipe 40 having an approximately 0.625" outer diameter and an approximately 0.527" inner diameter. Four 0.25" holes 41 are located on the underside of the stainless steel pipe 40. These holes 41 are capped with ¼ compression pieces 42. Unions 43 are included on either end of the stainless steel pipe 40. The cross-sectional view shows the outer filter housing 11, the housing annulus 12, the porous wall 13, and the porous filter element 14. All parts of the inertial filter 10 coming in contact with a gas sample are coated with a fused silica coating 15.

Figure 4:
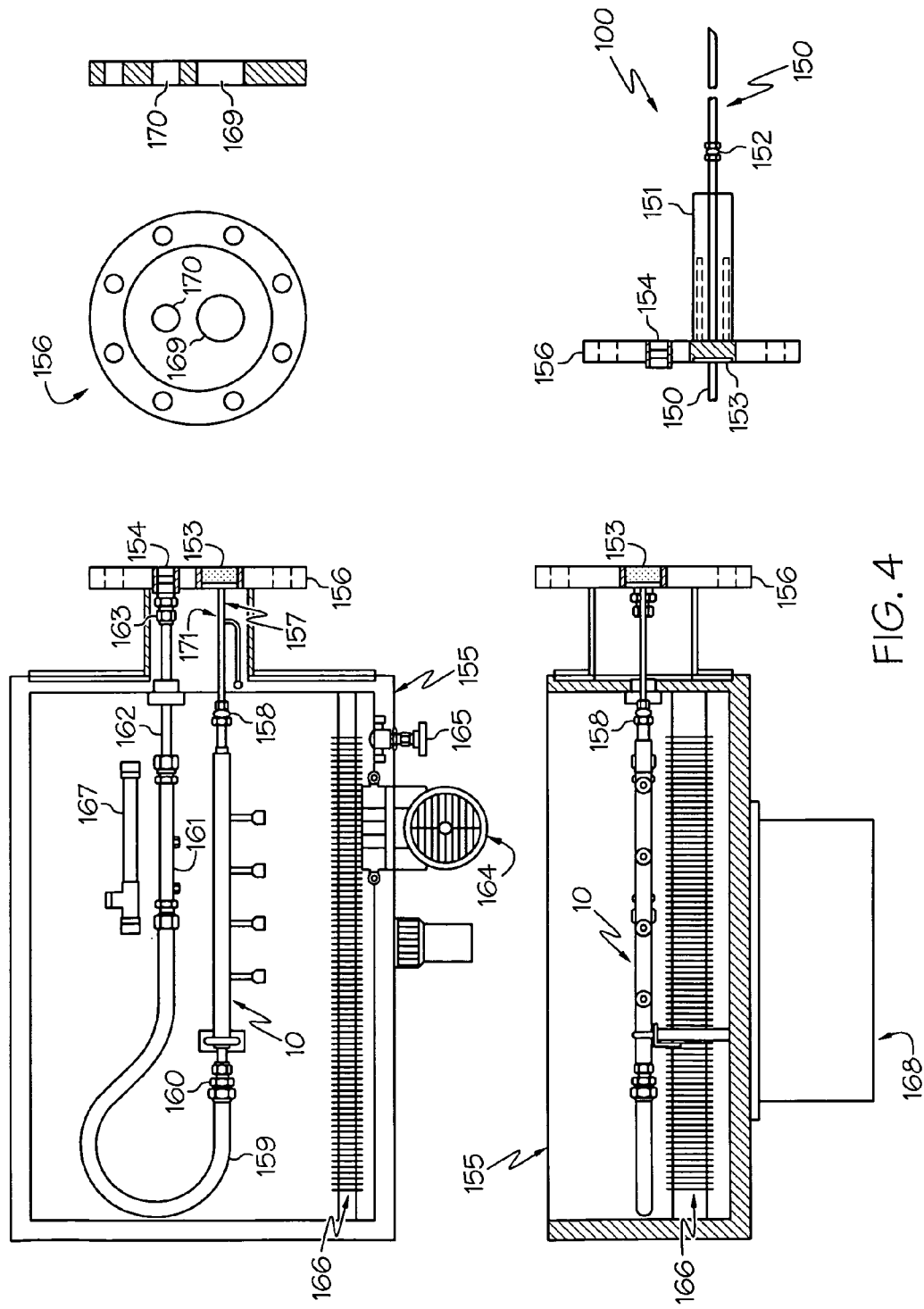
FIG. 4 is a door-side view and bottom view of the present gas sample acquisition and filtration apparatus.

A door-side view and bottom view of the preferred apparatus is shown in FIG. 4. A gas sample acquisition probe 100 is shown to contain a stainless steel stinger tip 150 joined to an aluminum stock 151 by a stainless steel compression unit 152. The gas sample acquisition probe is attached to a stainless steel mounting flange 156, and thus to the apparatus enclosure 155, via two couplings 153 and 154. The two couplings 153 and 154 are attached to the flange 156 via holes 169 and 170. The gas sample is transported into the inertial filter 10 by an inlet stainless steel sample tube 157, attached via a reducing union 158. A spike calibration gas tap 171 is located on the inlet sample tube 157 before attachment to the inertial filter 10. The gas sample leaves the inertial filter 10 via a stainless steel pipe 159, attached via a reducing union 160. The gas sample then passes through a venturi flow meter 161 under vacuum pressure. Finally, the gas sample leaves the apparatus enclosure 155 by passing through an eductor 162 and a male connector 163. The gas sample is powered through this system via a sample pump 164 and a needle valve 165. The temperature of the gas sample is maintained via a radiant heater 166 and/or a pre-heater 167. Attached to the apparatus enclosure 155 is a main control enclosure 168. Preferably, all parts coming in contact with a gas sample are coated with a fused silica coating 15.

Figure 5:
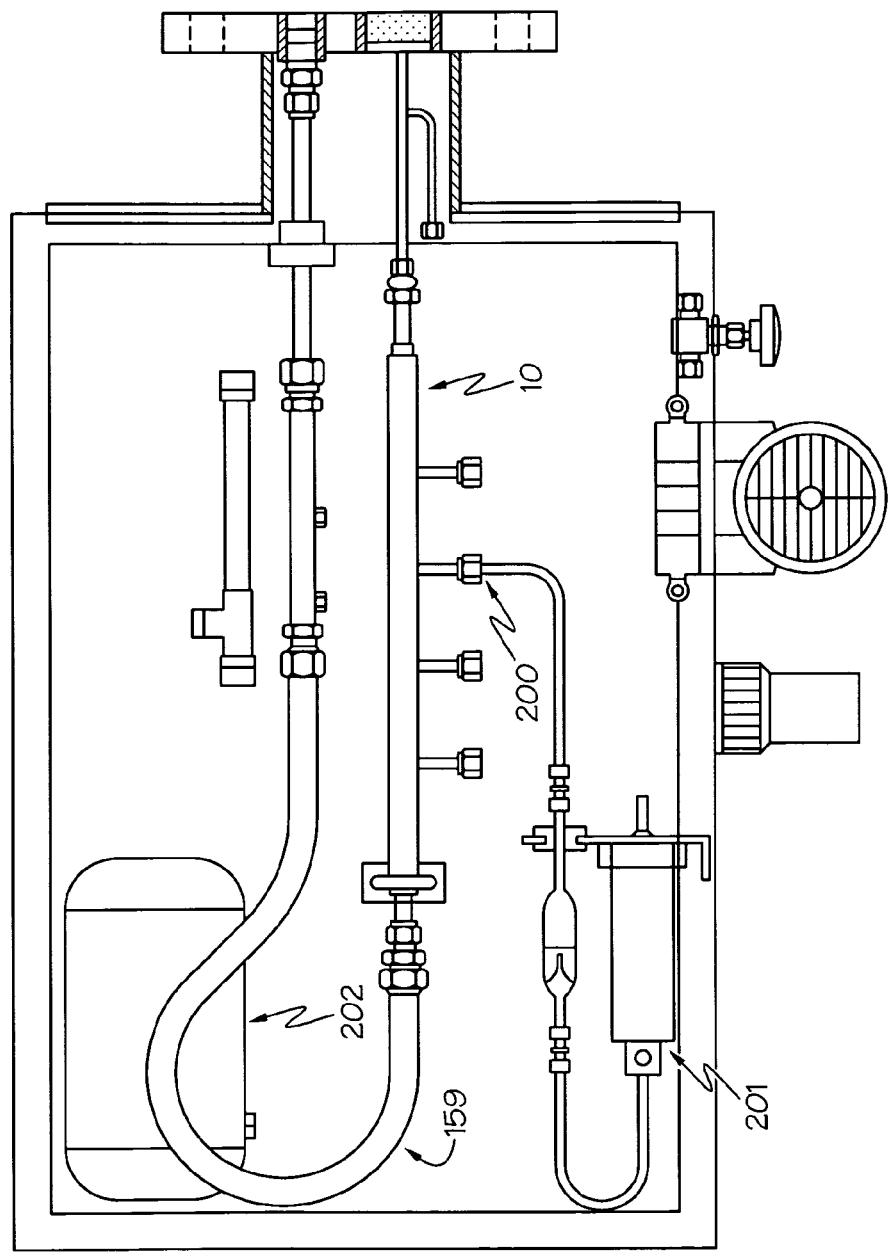
FIG. 5 is a door-side view of the present gas sample acquisition and filtration apparatus showing addition of a diluter assembly and an accumulator tank.

A door-side view of another preferred apparatus is shown in FIG. 5. In addition to the items shown in FIG. 4, in this embodiment the inertial filter 10 has a sample output 200 entering a secondary dilutor assembly 201. An accumulator tank 202 is fitted to provide high volume blowback air for fittings 20 and 171. All parts coming in contact with a gas sample are coated with a fused silica coating 15.

Figure 6:
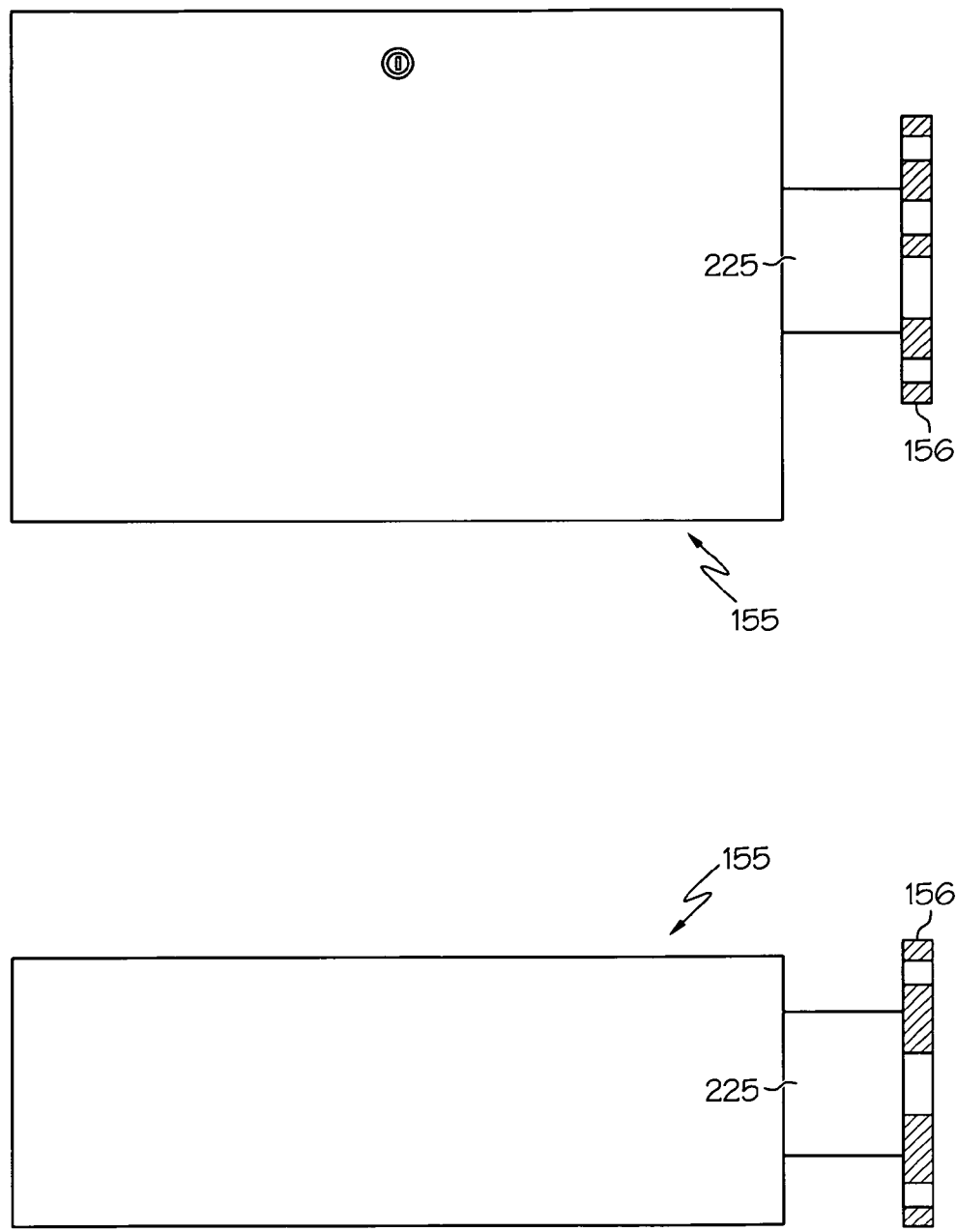
FIG. 6 is a door-side view and bottom view of an enclosure and mount for the present gas sample acquisition and filtration apparatus.

A door-side view and bottom view of the apparatus enclosure 155 and mounting flange 156 for the preferred apparatus is shown in FIG. 6. The mounting flange 156 is connected to the apparatus enclosure 155 via a pipe 225.

Static Filter

An apparatus using a static filter rather than an inertial filter to remove the particulates from the flue gas sample before measurement of the total gaseous mercury concentration is further contemplated herein. As with the inertial filter, the static filter will similarly contain a protective coating on all metal surfaces that may come into contact with the gas sample. In a particularly preferred embodiment, an apparatus using a static filter will additionally contain a diluter (coated with fused silica or a derivative thereof).

Figure 3:
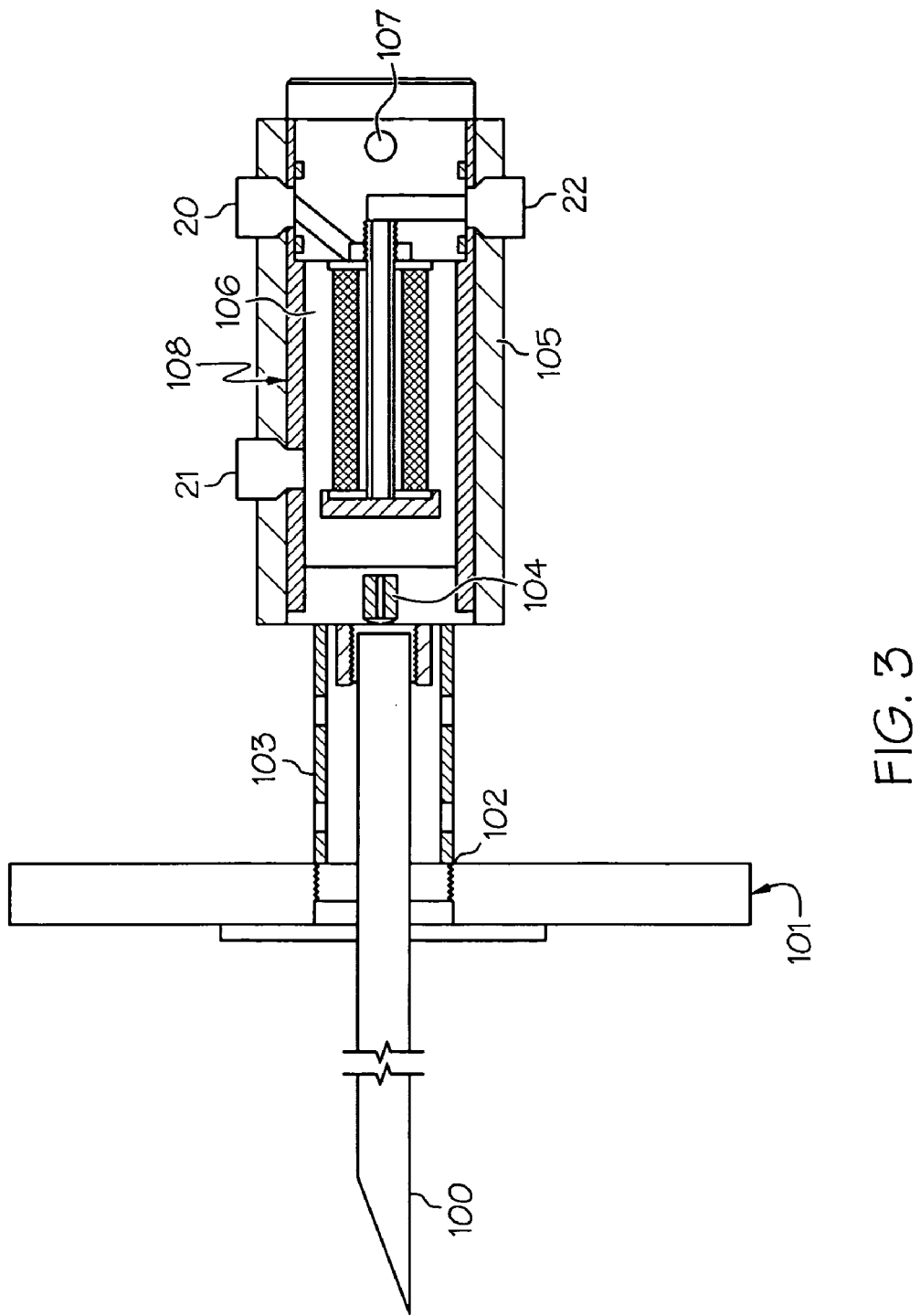
FIG. 3 is a diagram of the present static filter housing including a mounting flange and stringer that extends into the stack.

A sectional view of a preferred gas sample acquisition probe 100 and static filter housing 108 is shown in FIG. 3. The gas sample acquisition probe 100 is mounted to a stack wall 101 via a nipple 102. A sample heating nipple 103 surrounds the portion of the gas sample acquisition probe 100 outside the stack 101. Between the gas sample acquisition probe 100 and the static filter housing 108 is a vaporization chamber 104. A heater jacket 105 surrounds the static filter housing 108. Inside the static filter housing 108 is a sintered stainless steel filter media 106 having a fused silica coating 15. Also present on the static filter housing 108 are a blowback 20, a calibration gas input 21, and a sample output 22. The static filter housing 108 is kept in place by a special tube fitting 107. All parts coming in contact with a gas sample preferably are coated with a fused silica coating 15.

Figure 7:
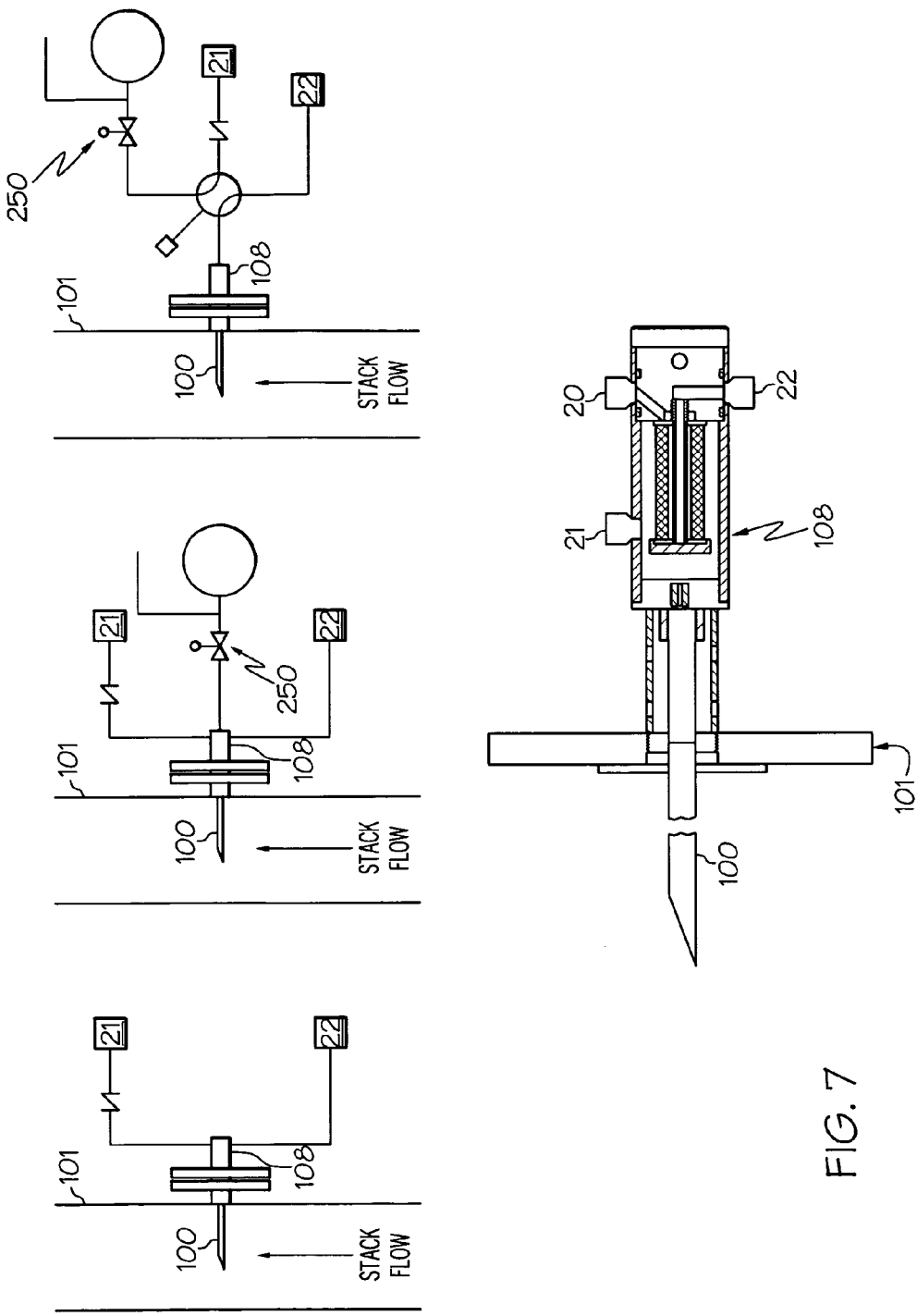
FIG. 7 is a plumbing diagram showing a sectional view of the static probe and three different plumbing arrangements for the static probe.

A plumbing diagram showing a sectional view of the gas sample acquisition probe 100 and static filter housing 108 and three different plumbing arrangements for the gas sample acquisition probe 100 and static filter housing 108 is shown in FIG. 7. The flow diagram indicates that flue gas flows up over the gas sample acquisition probe 100, which collects a gas sample. This gas sample enters the static filter housing 108 having a calibration gas input 21 and a sample gas output 22. The mass flow controller 250 is used to accurately measure a calibration gas volume injected into the sample flow.

Optimal Operating Conditions

It is desirable, but not required, to keep the inertial filter and associated sampling components at around 200° C. to ensure optimum accuracy in the measurement of total gaseous mercury concentration. At this temperature, the particulate material in the flue gas sample appears to have minimal effect on the integrity of the gas sample. Adsorption of oxidized mercury appears to be minimized and oxidation of elemental mercury to oxidized mercury is also minimized by the materials and compounds in the flue gas at this temperature.

Preparation of Preferred Apparatus

Three sizes of the porous filter element are preferable: approximately ½", ⅜", and ¼" inner diameter (ID) of a sintered metal filter media or ceramic filter media.

The entire flow path throughout the preferred apparatus is relatively smooth, with no gaps in the tubing of the assembly where particulate material can collect. Accordingly, the preferred apparatus provides a consistently laminar flow (smooth, undisturbed, quiet flow) of the sample past all of the inner tubing in contact with the flue gas sample. The particles are encouraged to move rapidly, in a vector parallel to the tubing wall surfaces, with minimum impingement, especially in the area of the porous filter element. In preferred embodiments, there should be no cracks, welds, or other disturbances in the continuity of the tubing in the flow path. Similarly, the sample gas temperature is maintained at or above the flue gas temperature being sampled to prevent moisture condensation, and importantly, $Hg^0$ and $Hg^{+2}$ deposition on the tubing walls. A temperature of approximately 200° C. or greater is particularly preferred in this regard.

The preferred inertial filter apparatus has 5 temperature-controlled zones:
 i. entire enclosure heaters;
 ii. heated stinger extension;
 iii. inertial filter body heater;
 iv. eductor air preheater; and
 v. diluter assembly, when fitted.

The heated filter probe extension, where the stinger, or gas sample acquisition probe 100 (probe tubing extending into the stack) is attached, uses a tube union. The ID of the stinger matches the ID of the heated inlet tubing. Stingers are usually approximately 36" to approximately 80" in length, coated with a fused silica 15 to prevent deposition of $Hg^0$ and $Hg^{+2}$. This heated extension surrounds the sample inlet tubing to heat the incoming gas to approximately 200° C. The heated extension is approximately 6" long or longer, and preferably heated with one cartridge type heater, watt capacity sized to fit the application. For some applications where there is a stack liner, the heated extension runs the entire length between the mounting flange 156 and the stack inside wall surface 101. The cartridge heater is controlled by a PID, thermocouple, or RTD controller, according to user preference. For longer heated extensions, preheated air is circulated inside the extension to maintain the temperature at approximately 200° C.

The incoming sample tubing 157 ID matches the ID of the porous filter element 14. This tubing, approximately 15" long, extends through the heated extension into the apparatus enclosure 155, ending in a tube union 158 attached to the porous interior of the inertial filter 10. Welded into this inlet tubing is an about ¼" spike calibration gas inlet tube, welded to the sample inlet tubing as close to the mounting flange area as possible. There is an about 6 inch run of inlet sample tubing after this weld tee, to allow for sufficient calibration gas mixing, prior to the stack gas/calibration gas mixture entering the porous filter element 14 section of the inertial filter 10. Preferably, all metal surfaces, including the stinger 100, tube unions (e.g., 158 and 160), inlet tubing (157) run with calibration tee, porous filter element 14, and inertial filter 10, are coated with fused silica 15 to prevent absorption or chemical changes in $Hg^0$ to $Hg^{+2}$ ratios.

The porous filter element 14 length is nominally set from about 12 to about 24 inches of filter length. This length can vary depending upon take-off sample flow rates desired by the analysis system. The sample take-off axial velocity should not exceed about 0.006 fps. The fast loop flow design specifications for each size filter is:
 i. ½": 0 to 300 liters/minute;
 ii. ⅜": 0 to 200 liters/minute; and
 iii. ¼": 0 to 100 liters/minute.

The fast loop and bypass flow rates are calculated to produce 70-100 fps gas velocity through the porous filter element 14. Particularly preferred is an apparatus that maintains a 10,000:1 fast loop, bypass to sample take-off velocity.

A special inlet tubing fitting 43 centers the porous filter element 14 into the inlet and outlet sample tubing to provide a uniform, smooth ID tube without any breaks or cracks, both coated with fused silica 15, prior to welding up the inertial filter 10. An outer tube 11 surrounds the porous filter element 14, which has an outer diameter (OD) sized to provide an about 0.0625" annular space between outer tube ID and porous filter element OD. All surfaces are coated with fused silica 15 prior to welding up the apparatus, which coating is preferably repeated after welding.

There are approximately five about ¼" tubing taps on the inertial filter apparatus 10.
 1. The first tap is the spike calibration gas tap 171 on the inlet sample tubing 157 close to the mounting flange 156.
 2. There are four about ¼" tubing taps 41 on the side of the annular tubing 11 surrounding the porous filter element 14. These taps are for:
  1. a blow back air inlet 20;
  2. a calibration gas input 21;
  3. a sample output 22; and
  4. a filter surface temperature thermocouple or RTD 23.

All tubing downstream of the porous filter element 14 maintains the smooth inner bore without breaks, cracks, or ID changes. These surfaces do not have to be coated with fused silica since the sample has already been taken.

There is an about 180° loop in the tubing to return the fast loop bypassed sample to the front of the apparatus enclosure 155. The next component in the piping is a venturi 161, specifically designed for the flow ranges given above for a gas density of stack gas of approximately 29 molecular weight, with upstream and downstream pressure taps to provide a pressure drop output. Using NIST traceable calibration curve, the user can determine the total flow for the fast loop, bypassed sample gas flow. This factor is required to measure the dilution occurring when calibration gas is injected into the inlet sample tubing about ¼" calibration inlet 171, for the "spike" calibration required by the EPA to assess the transport performance of $Hg^0$ to $Hg^{+2}$ through the porous filter element 14. Accordingly, this will allow for the measurement of the $Hg^0$ to $Hg^{+2}$ mercury species only, and not the particulate bound mercury.

The venturi's 161 inlet and outlet connection are welded tubing, with the inlet and outlet of the venturi 161 machined to accept a tubing butt fit for smooth bore flow, to prevent particulate material from accumulating.

Downstream of the venturi 161 is an air powered eductor 162 with the same tubing ID and induced flow range, with about 100 psig supply air pressure, to produce the fast loop, bypass flue gas sample flow rates listed above.

The motive power air passes through an air pre-heater 167, electrically powered and controlled, with sufficient wattage to produce exit air at a temperature greater than about 150° C. to the eductor 162.

The purpose of the eductor air preheater 167 is to prevent water condensation in the body of the eductor 162, which would result in stack gas particles agglomerating in the eductor 162, reducing flow and efficiency of the eductor 162.

All four (4) temperature-control zones installed in the Mercury Inertial Filter Assembly have bimetallic overtemp switches for circuit protection.

Blowback Assembly

In addition to high velocities through the porous filter element 14 of the inertial filter 10, a high-pressure air backpurge, or blowback assembly, is installed.

All components of the blowback assembly are mounted within the heated zone, except for the control solenoid (solenoids). These valves are mounted in an externally mounted enclosure 168 at ambient temperature. Included is a stainless steel pressure vessel, preferably about 1-liter, for accumulating back purge to a volume of about 10 liters at a pressure of about 90 psig.

The stored air, heated by the stainless tank mounted in the 200° C. enclosure zone, flows from storage through the two way blowback solenoid to the blowback tubing connection on the inertial filter 10. This blowback backpurges the filter.

Some applications may require backpurging the high speed, bypass sample piping, and the gas sample acquisition probe 100. In this regard, a 3-way solenoid preferably is mounted in the external enclosure 168 to control the direction of the hot backpurge air either to the porous filter blowback fitting, or to the calibration gas spike tubing fitting.

Sample Pump

A diaphragm heated head sample pump 164 is mounted integral within the apparatus enclosure 155. All surfaces in contact with the sample are either Teflon® or fused silica coated stainless steel or Hastelloy. An extended head from the sample pump 164 extends into the heated zone to maintain an operating head temperature of at least about 200° C.

The sample pump 164 is connected directly to the sample out tubing 22 mounted on the inertial filter 10. Occasionally, a particulate filter, sub micron, glass, is fitted in the tubing 159 between the sample out tubing 22 and the sample pump 164 inlet. In a speciating Hg inertial filter apparatus, a $Hg^{+2}$ reducer is fitted in between the inertial filter sample outlet and the sample pump inlet.

When a Diluter Assembly 201 is fitted to the inertial filter apparatus 10, the sample pump 164 is not fitted. The $Hg^{+2}$ reducer is fitted after the Diluter Assembly 201 to decrease the reduction load on the reducer assembly.

Mercury Inertial Filter Assembly Outlet Connection

The inertial filter 10 is fitted with a heated sample line boot assembly. This sample line boot assembly can be about 1½" to 2½" in diameter, and has a heat shrink section to fuse to the heated sample line surface, sealing the apparatus enclosure 155 from ambient air. All field connections to the inertial filter 10 enter the heated zone through this boot. The heated sample line contains: an about ¼" PFA Teflon® sample line; an about ¼" PFA Teflon® air supply line; an about ¼" PFA Teflon® calibration gas line; messenger wires to power the assembly; and digital messenger wires for monitoring and control.

The PFA Teflon® sample line is connected to the sample out tubing connector mounted on the sample pump head.

Diluter Assembly for the Hg Inertial Filter Assembly

Some process and flue gas applications require a dilution of the existing $Hg^0$ to $Hg^{+2}$ species. Dilution of the sample gas occurs in this diluter assembly 201, in ratios ranging from about 13:1 to about 250:1.

All metallic surfaces of the diluter assembly 201 are coated with fused silica 15 to prevent mercury speciation changes or adsorption.

The diluter assembly 201 is connected directly to the inertial filter outlet tubing using a fused silica 15 coated tube union. The diluter assembly 201 consists of a glass precision orifice, mounted in a holder with an "O" ring and tube fitting. This sample precision orifice is mounted directly onto the body of the dilution eductor.

The diluted sample then exits the inertial filter 10 via a fused silica 15 coated bulkhead fitting. Tubing from the outlet of the dilution eductor to the bulkhead fitting is PFA Teflon®.

Calibrators

Calibrators for generating $Hg^0$ to $Hg^{+2}$ concentrations directly into the inertial filter 10 are fitted directly onto the exterior surface of the heated inertial filter 10.

Oxygen Sensor

Under certain circumstances, either by application, EPA Federal requirement, or local APCD demand, an oxygen sensor (Diluent Analyzer) may be installed in the inertial filter 10.

This Diluent Analyzer is mounted integrally within the apparatus enclosure 155 or directly attached to the exterior surface of the apparatus enclosure 155.

Depending upon application, the measurement of this oxygen sensor will be on either a wet basis or a dry basis, using a thermo-electric (TE) chiller.

Sample Transport and Conditioning System.

Dry Basis Sample Transport and Conditioning System

A heated sample line, operating at a temperature of about 200° C., connects the inertial filter 10 with the remaining sample conditioning system. This heated sample transport line terminates at a thermoelectric (TE) sample gas chiller to remove water. The TE chiller is fitted with removable impingers, and all surfaces are coated with fused silica 15, and sealed with a Viton "0" ring. The impingers are designed to rapidly separate water from sample gas to minimize mercury contact with the condensed water.

Water is removed via a peristaltic drain pump with tubing and RPM sized to fit the application. The sample gas exits the TE chiller and passes to the downstream mercury analysis system. No flowmeters, filters, or other components are fitted into the flow stream, in order to minimize components and surface area, which results in $Hg^0$ loss.

Wet Basis Sample Transport System

When a diluter is fitted into the inertial filter 10, no other sample conditioning components are required. A frost-free, ¼" PFA Teflon® sample line is connected between the inertial filter 10 and the downstream mercury analysis system.

A preferred heated gas sample acquisition and static filtration apparatus is designed for mounting on a stack or duct. Its primary function is to collect a flue gas sample, provide a heated environment to maintain sample gas temperatures above dewpoint, and remove particulate material from the gas sample. This heated gas sample acquisition and static filtration apparatus contains a standard 10 or 50 micron sintered stainless steel filter media, a circuit board regulated heater jacket, an integral calibration gas port on both sides of the filter media, a NEMA 4 enclosure, and a circuit board controlled blowback system to clean the filter media.

The general specifications for this heated gas sample acquisition and static filtration apparatus are as follows:

| | |
|---|---|
| Probe | 18" Stinger probe, 0.5" diameter × 0.065" wall, 316 L tubing |
| Calibration | Integral calibration on both sides of filter element |
| Heater Jacket | Circuit board regulated |
| Connections | 1¼" male pipe nipple mount; ½" male pipe thread adapter |
| Connectors | ¼" cal gas, ¼" sample line |
| Thermocouple | Type K |
| Blowback | Single direct; 2-way solenoid blowback/calibration valve |
| Blowback Tank | 16 gallon stainless steel, 4" × 8", leak checked, pressure tested |
| Heat-shrink Boot | 7" length, 2.75" minimum expanded ID nose |
| O-rings | Viton ® |

-continued

| | |
|---|---|
| Gaskets | Graphoil or Silicone |
| Dimensions | 14" × 12" × 8" HWD (w/out Stinger probe) |
| Weight | 34 lbs. |

Similarly, the operating specifications for this heated gas sample acquisition and static filtration apparatus are as follows:

| | |
|---|---|
| Sample Flow Rate | 6-10 LPM |
| Calibration Gas Requirement | 20 psig, 6-10 LPM |
| Probe Operating Temperature | 375° F. (190° C.) |
| Input Voltage | 90-260 VAC, 50/60 Hz |
| Blowback Duration | 5 sec standard (30 sec maximum) |
| Blowback Frequency | Every 24 hours standard (range 10 minutes to 99 hours) |
| Blowback Valve | 12 or 24 VDC, 115 or 230 VAC, 100 psig max pressure |
| Blowback Flowrate | 14 scfh |
| Instrument Air for Blowback | Min 50 psig, Max 90 psig |

Likewise, the material specifications for this heated gas sample acquisition and static filtration apparatus are as follows:

| | |
|---|---|
| Enclosure Material | NEMA 4 |
| Heater Type | Silicone rubber blanket with snap closures |
| Oven Insulation Material | ⅛" thick silicone, medium density |
| Filter Chamber Material | 316 stainless steel |
| Filter Element Types | 2 micron ceramic<br>5, 10, 20 micron sintered SS<br>2 micron SS screen mesh |

The probe is preferably coated with a fused silica or derivative thereof protective coating to prevent corrosion, gas absorption, or gas reaction with the stainless steel construction of the probe.

Gas Analyzer

Once the gas sample has been collected and conditioned by the preferred gas sample acquisition and filtration apparatus, the sample will pass to a gas analyzer, where the total gaseous mercury concentration, including concentration of $Hg^0$ and $Hg^{+2}$ individually, is measured. Suitable gas analyzers are well known in the art and include, without limitation, UV atomic absorption or atomic fluorescence detectors.

Preferred Processes

A preferred aspect further relates to a process for accurately measuring total gaseous mercury concentration in flue gas comprising the steps of:
(1) removing a gas sample from flue gas containing gaseous mercury using a gas sample acquisition probe;
(2) passing said gas sample into an inertial filter comprising a porous filter element to remove particulate material present in said gas sample, wherein all metal surfaces of said inertial filter are coated with a protective coating; and
(3) measuring the amount of gaseous mercury present in said gas sample.

In a preferred embodiment, all metal surfaces of the gas sample acquisition probe coming into contact with the flue gas are coated with a protective coating. In a preferred embodiment, the protective coating is comprised of fused silica or a fused silica derivative. The protective coating can have a thickness of up to about several thousand Angstroms. Further, the protective coating reduces chemical reactivity to the gaseous mercury of all of the metal surfaces coming into contact with the gas sample without impeding gas flow through the inertial filter. The process chemical reactions reduced on said metal surfaces according to the preferred processes comprise oxidation of elemental mercury to a chemically combined form of mercury and loss of oxidized mercury through adsorption on said metal surfaces. Accordingly, the preferred processes do not chemically alter gaseous mercury present in the gas sample passing through the inertial filter.

In another preferred embodiment, these processes permit the measurement of gaseous mercury selected from the group consisting of $Hg^{+2}$, $Hg^0$, and a combination thereof. Accordingly, these processes are capable of determining how much of the total gaseous mercury concentration is present in the flue gas as $Hg^{+2}$ and how much of the total gaseous mercury concentration is present in the flue gas as $Hg^0$.

Preferred processes insert a gas sample acquisition probe (stinger) into the flue gas to take the gas sample. This gas sample is then maintained at a temperature greater than or equal to the temperature of the flue gas. The gas sample can be taken from the flue gas before the flue gas passes through an electrostatic precipitator (ESP); after the flue gas passes through an ESP; before the flue gas passes through a wet scrubber; after the flue gas passes through a wet scrubber; before the flue gas passes through a flue gas desulfurization device (FGD); after the flue gas passes through an FGD; or from final flue gas passing through a smoke stack. Accordingly, preferred processes accurately measure total mercury concentrations, both $Hg^0$ and $Hg^{+2}$, in a gas sample taken from any of these sampling locations typically found in coal fired power plant processes.

EXAMPLES

Numerous tests have verified the unexpectedly advantageous properties of the preferred apparatus, most notably those conducted by Sjostrom et al. relating to an initial version of a preferred apparatus. In some of these tests, coated parts have been substituted for uncoated parts in mercury sampling systems as a basis for comparison. In all cases, the total gaseous mercury recovered improved and the integrity of the ratio of elemental to oxidized mercury was better preserved when exposed to the coated parts.

Two systems were used to introduce elemental and oxidized mercury into the probe extension upstream of the gas sample acquisition and filtration apparatus during testing. The elemental spiking system was a PSA 10.534 Mercury Calibration System fabricated by PS Analytical. The PSA 10.534 provides a wide range of mercury concentrations by altering the temperature of a mercury reservoir and varying the gas flowrate through the reservoir. The mercury reservoir is constructed by impregnating elemental mercury on an inert substrate. The gas passing over the reservoir becomes saturated with mercury at the reservoir temperature.

The oxidized mercury source was a Hot-Vapor Calibration (HOVACAL) system manufactured by IAS GmbH. For this system, a solution of mercuric chloride is injected onto a heated head to evaporate the solution. Nitrogen carries the gaseous mercuric chloride into the bulk gas. The liquid calibration solution is delivered to the head with a peristaltic pump. The flow rate of the pump is confirmed using a loss-of-weight balance. The peristaltic pump feed rate, the nitrogen flow rate, and the head temperature are controlled with the touch-screen interface shown on the front of the HOVACAL unit.

The goal of the evaluation program was to test three inertial probes in order to determine the effectiveness of the inertial filter to transport both elemental and oxidized mercury in a relatively clean gas stream. The inertial probe apparatuses tested were:

A) Large Inertial Probe apparatus with fused silica coating on all sample contact surfaces.

B) Large Inertial Probe apparatus with no fused silica coating.

C) Small Inertial Probe apparatus with no fused silica coating.

A further goal of this evaluation program was to quantitatively assess the ability to inertially separate particles with a high affinity for mercury with minimal sampling artifacts. The general plan was to spike the probes with elemental mercury and measure quantitatively how much of the mercury passes through the filter.

Probe Preparation

Flow Measurement

The oxidized and elemental spiking systems were configured to introduce a small volume, concentrated stream of vapor-phase mercury into the bulk probe flow upstream of the inertial filter. The flow through the filter must be monitored to determine the predicted mercury concentration in the bulk flow downstream of spiking.

Each apparatus was retrofitted with a venturi flow meter prior to installation to monitor the flow through the apparatus. The venturi flow meters were added to the end of the exhaust return pipe on the apparatus to eliminate the need to modify the overall apparatus design or operation. Compressed air is introduced into the vacuum eductors upstream of the exhaust venturis. Therefore, the compressed air flow was also monitored to determine the flow through the inertial filter portion of the gas sample acquisition and filtration apparatus. Two of the apparatuses also included integral venturi flow meters.

Calibration Ports

The Apogee and Thermo apparatuses were retrofitted with calibration taps immediately upstream of the inertial filter to allow spiking with elemental and oxidized mercury. The length of the calibration line was minimized to prevent losses of $HgCl_2$ in calibration line upstream of the apparatus.

Probe Extensions (Stingers)

A 6-foot fused silica coated stinger was installed on the inlet of each extraction probe. For the two higher flow apparatuses, ¾" pipe was used. One-half inch tube was used for the stinger on the lower-flow apparatus.

Activated Carbon Injection Line

A ¼-inch stainless steel carrier line was installed along the stinger. One end of this line extended into the tip of the stinger. The opposite end of this line terminated at the flange to allow doping with activated carbon.

Test Protocol

The exhaust venturi flow meters and integral venturi flow meters were calibrated using a laminar flow element prior to testing. These calibrations were used to determine the expected vapor-phase spike concentrations during elemental and oxidized spiking periods. The apparatuses were installed and operating at the manufacturers recommended operating conditions (flow and temperature) at least 24 hours before initiating testing.

At the beginning of each test day, the instruments were calibrated with the on-board permeation device. Following calibration, baseline mercury measurements were made to establish the vapor-phase mercury concentration and speciation in the duct. A PRB coal was tested. The mercury concentration was fairly stable and the mercury was primarily in the elemental form (typically >80%).

After establishing the baseline conditions, the output from the PSA 10.534 was connected to the calibration port on the extraction probe. Based upon the saturator temperature and flowrate through the PSA 10.534, the mercury introduced to the probe (ng/min) could be calculated. The concentration of mercury expected was determined by adding the mercury mass injection rate divided by the probe flow to the baseline duct concentration. Each apparatus was evaluated at 300 and 400° F.

Following performance evaluations with elemental mercury, the apparatuses were spiked with oxidized mercury from the HOVACAL system. The concentration of oxidized mercury was calculated using the injection rate of the $HgCl_2$ solution and the flow rate through the apparatus. Tests were conducted at 300 and 400° F. to establish the temperature stability of the apparatuses for oxidized mercury measurements.

The final test was designed to determine the inertial separation effectiveness. Because the three apparatuses were installed at the outlet of the electrostatic precipitator, the fly ash loading to the apparatuses was quite low. This provided a good opportunity to evaluate the apparatus for elemental and oxidized mercury measurements without concern for in-duct reactions with the fly ash. However, this test location and particular fly ash (relatively low mercury removal effectiveness) did not challenge the apparatuses for their ability to adequately separate particulate matter while minimizing the sampling artifacts.

For the final test, NORIT FGD activated carbon was introduced by batch injection into the tip of the probe extension. The injection rate was equivalent to nominally 45 lb/MMacf, which is roughly twice the maximum injection rate economically feasible for an ESP application. The injection was maintained for 30 seconds and repeated at two different apparatus operating temperatures (300 and 400° F.). Total and elemental mercury measurements were made during and following injection. The residence time in the probe extensions was less than 0.15 seconds for most of the test conditions.

Results

The baseline vapor-phase mercury concentration in the flue gas during testing ranged from 9 to 12 µg/Nm³. The flue gas flowrate through the larger apparatuses ranged from 10 to 11.5 acfm. The flowrate through the smaller apparatus ranged from 2.25 to 3.0 acfm. The large apparatuses were operated at their maximum design velocity and the small apparatus was operated slightly above the design velocity of the system.

Elemental Mercury Spiking

All three apparatuses performed well when elemental mercury was introduced upstream of the inertial filter. The recovery of total mercury was quite good and well within the measurement uncertainty of the apparatus flow. Both uncoated stainless steel apparatuses demonstrated some oxidation. The larger apparatus demonstrated somewhat more oxidation (11% at 300° F. and 19% at 400° F.). The smaller uncoated apparatus demonstrated slight (3 to 5%) oxidation at 300 to 400° F. The fused silica coated apparatus did not demonstrate any measurable oxidation at either temperature.

Oxidized Mercury Spiking

High concentrations of oxidized mercury can be difficult to transport. During spiking with oxidized mercury, care was taken to assure spike transport lines were as short as possible and to maintain the transport lines at the temperature of the apparatus. The spiking port on two of the apparatuses (the small apparatus and one of the larger apparatuses) was retrofitted so that the HOVACAL head could be connected directly to the port. The calibration port for the other large apparatus was located inside the heated enclosure requiring nominally 18-inches of PFA Teflon® and 6-inches of coated stainless steel transport line prior to entering the bulk probe flow.

The recovery of oxidized mercury was very good (>90% of the expected concentration) on both apparatus that could be close coupled to the HOVACAL head. For the larger apparatus, the recovery was slightly lower at 300° F. than 400° F. There was no measurable difference in performance between 300 and 400° F. for the smaller apparatus. The smaller apparatus also resulted in a higher fraction of the sample measured as oxidized (>95% of expected). The oxidized mercury measured with the larger apparatus was 82 to 85% of the expected concentration.

The oxidized mercury spike test for the apparatus with the calibration port extension was not as successful as the other two apparatuses. Nominally 50% of the spiked concentration was measured when using this apparatus, and only 30 to 40% of the expected concentration was measured as oxidized mercury. Due to the difficulties transporting oxidized mercury, it is suspected that the poor performance was due to difficulties transporting the spike sample to the calibration port on the apparatus and not necessarily due to any other aspect of the apparatus design. Modifications to allow direct coupling of the HOVACAL head to this apparatus are required to allow an appropriate evaluation of oxidized mercury spiking.

Doping with Activated Carbon

Each of the apparatuses was challenged with activated carbon following characterization with elemental and oxidized mercury to qualitatively assess the ability of the apparatuses to inertially separate particulate matter with an affinity for mercury.

Both large apparatuses demonstrated a rapid drop in mercury concentration following injection. The concentration immediately following injection was 15 to 60% lower than the initial concentration. The total mercury concentration on one of the large (uncoated) apparatuses returned immediately to the baseline concentration following injection. However, some activated carbon remained on the filter as evidenced by the increased oxidation across the apparatus (typically 20% additional oxidation following injection).

The total mercury concentration measured with the coated apparatus did not immediately return to baseline concentrations but remained suppressed to up to an hour following doping with powder activated carbon (PAC). This PAC is iodized to enhance its affinity for Hg species. The PAC is intentionally injected to adsorb Hg species onto its surface, and be removed in a downstream COHPAC baghouse, and finally discarded with the flash. The fraction of oxidized mercury also increased across this probe following each injection episode. The preferred apparatus should not hang up carbon as the operator will use the inertial filter to control the carbon injection rate.

No drop in mercury concentration or increase in oxidation was noted across the small apparatus.

It is important to note, however, that this activated carbon test does not accurately represent typical plant operating conditions under which the preferred apparatus would be expected to perform. Most power plant operators do not want to emit any excess carbon as this includes unburned fuel. In fact, many utilities have monitors to detect and control carbon levels. Accordingly, the preferred apparatus, when used in such industrial applications, would avoid significant problems related to mercury being trapped on excess carbon.

Additionally, this test was conducted on an embodiment of the present apparatus that did not contain the unions 43. A preferred apparatus containing the unions 43 would not exhibit this Hg attenuation. Accordingly, the above-described area that collected carbon would not be present in the preferred apparatus.

The foregoing is a detailed description of preferred embodiments. It will be apparent that the same may be modified or varied in many ways. Such modifications and variations are not to be regarded as a departure from the spirit and scope of the inventive subject matter, and all such modifications and variations are intended to be included within the scope of the following claims.

We claim:

1. An apparatus for measuring mercury concentration in a flue gas, the apparatus comprising a gas sample acquisition probe, an inertial filter, and an analyzer, wherein:
   the gas sample acquisition probe is configured to initiate transport of a gas sample from the flue gas to the inertial filter;
   the inertial filter comprises a porous filter element that removes particulate material from the gas sample and outputs a filtered gas sample;
   the analyzer measures the amount of gaseous mercury present in the filtered gas sample;
   the inertial filter comprises metal surfaces that are coated with a protective coating that reduces chemical reactivity of the metal surfaces to gaseous mercury;
   the protective coating comprises fused silica or a derivative thereof and the coated metal surfaces are further coated with a secondary chemical deactivation layer configured to cover silanol groups on the surface of the protective coating; and
   the coated filter surfaces are positioned to contact a gas sample flowing through the filter.

2. An apparatus for measuring mercury concentration in a flue gas, the apparatus comprising a gas sample acquisition probe, an inertial filter, and an analyzer, wherein:
   the gas sample acquisition probe is configured to initiate transport of a gas sample from the flue gas to the inertial filter;
   the inertial filter comprises a porous filter element that removes particulate material from the gas sample and outputs a filtered gas sample;
   the analyzer measures the amount of gaseous mercury present in the filtered gas sample;

the inertial filter comprises metal surfaces that are coated with a protective coating that reduces chemical reactivity of the metal surfaces to gaseous mercury;
the protective coating comprises a polymer; and
the coated filter surfaces are positioned to contact a gas sample flowing through the filter.

3. An apparatus as claimed in claim 2 wherein the polymeric protective coating comprises a plurality of polymeric layers bonded to the metal surfaces.

4. An apparatus for measuring mercury concentration in a flue gas, the apparatus comprising a gas sample acquisition probe, an inertial filter, and an analyzer, wherein:
the gas sample acquisition probe is configured to initiate transport of a gas sample from the flue gas to the inertial filter;
the inertial filter comprises a porous filter element that removes particulate material from the gas sample and outputs a filtered gas sample;
the analyzer measures the amount of gaseous mercury present in the filtered gas sample;
the inertial filter comprises metal surfaces that are coated with a protective coating that reduces chemical reactivity of the metal surfaces to gaseous mercury;
the protective coating has a thickness of up to approximately several thousand Angstroms; and
the coated filter surfaces are positioned to contact a gas sample flowing through the filter.

5. An apparatus for measuring mercury concentration in a flue gas, the apparatus comprising a gas sample acquisition probe, an inertial filter, and an analyzer, wherein:
the gas sample acquisition probe is configured to initiate transport of a gas sample from the flue gas to the inertial filter;
the inertial filter comprises a porous filter element that removes particulate material from the gas sample and outputs a filtered gas sample;
the analyzer measures the amount of gaseous mercury present in the filtered gas sample;
the inertial filter comprises metal surfaces that are coated with a protective coating that reduces chemical reactivity of the metal surfaces to gaseous mercury;
the thickness of the protective coating is limited to a few molecules; and
the coated filter surfaces are positioned to contact a gas sample flowing through the filter.

6. An apparatus for measuring mercury concentration in a flue gas, the apparatus comprising a gas sample acquisition probe, an inertial filter, and an analyzer, wherein:
the gas sample acquisition probe is configured to initiate transport of a gas sample from the flue gas to the inertial filter;
the inertial filter comprises a porous filter element that removes particulate material from the gas sample and outputs a filtered gas sample;
the analyzer measures the amount of gaseous mercury present in the filtered gas sample;
the inertial filter comprises metal surfaces that are coated with a protective coating that reduces chemical reactivity of the metal surfaces to gaseous mercury;
the thickness of the protective coating is such that the porous filter element defines pore size from about 0.1 microns to about 50 microns absent the protective coating and a pore size from 0.1 microns to about 0.5 microns with the protective coating; and
the coated filter surfaces are positioned to contact a gas sample flowing through the filter.

7. An apparatus for measuring mercury concentration in a flue gas, the apparatus comprising a gas sample acquisition probe, an inertial filter, and an analyzer, wherein:
the gas sample acquisition probe is configured to initiate transport of a gas sample from the flue gas to the inertial filter;
the inertial filter comprises a porous filter element that removes particulate material from the gas sample and outputs a filtered gas sample;
the analyzer measures the amount of gaseous mercury present in the filtered gas sample;
the inertial filter comprises metal surfaces that are coated with a protective coating that reduces chemical reactivity of the metal surfaces to gaseous mercury;
the chemical reactivity of the metal surfaces that is reduced comprises oxidation of elemental mercury to a chemically combined form of mercury and loss of oxidized mercury through adsorption on the metal surfaces; and
the coated filter surfaces are positioned to contact a gas sample flowing through the filter.

8. An apparatus for measuring mercury concentration in a flue gas, the apparatus comprising a gas sample acquisition probe, an inertial filter, and an analyzer, wherein:
the gas sample acquisition probe is configured to initiate transport of a gas sample from the flue gas to the inertial filter;
the inertial filter comprises a porous filter element that removes particulate material from the gas sample and outputs a filtered gas sample;
the analyzer measures the amount of gaseous mercury present in the filtered gas sample;
the inertial filter comprises metal surfaces that are coated with a protective coating that reduces chemical reactivity of the metal surfaces to gaseous mercury;
the protective coating prevents chemical alteration of the gaseous mercury present in the sample gas passing through the inertial filter; and
the coated filter surfaces are positioned to contact a gas sample flowing through the filter.

9. An apparatus for measuring mercury concentration in a flue gas, the apparatus comprising a gas sample acquisition probe, an inertial filter, and an analyzer, wherein:
the gas sample acquisition probe is configured to initiate transport of a gas sample from the flue gas to the inertial filter;
the inertial filter comprises a porous filter element that removes particulate material from the gas sample and outputs a filtered gas sample;
the analyzer measures the amount of gaseous mercury present in the filtered gas sample;
the inertial filter comprises metal surfaces that are coated with a protective coating that reduces chemical reactivity of the metal surfaces to gaseous mercury;
the gaseous mercury measured in the particulate free gas sample is selected from the group consisting of $Hg^{+2}$, $Hg^0$, and a combination thereof; and
the coated filter surfaces are positioned to contact a gas sample flowing through the filter.

10. An apparatus for measuring mercury concentration in a flue gas, the apparatus comprising a gas sample acquisition probe, an inertial filter, and an analyzer, wherein:
the gas sample acquisition probe is configured to initiate transport of a gas sample from the flue gas to the inertial filter;
the porous filter element comprises a ceramic filter media;

the inertial filter comprises a porous filter element that removes particulate material from the gas sample and outputs a filtered gas sample;

the analyzer measures the amount of gaseous mercury present in the filtered gas sample;

the inertial filter comprises metal surfaces that are coated with a protective coating that reduces chemical reactivity of the metal surfaces to gaseous mercury; and the coated filter surfaces are positioned to contact a gas sample flowing through the filter.

11. An apparatus for measuring mercury concentration in a flue gas, the apparatus comprising a gas sample acquisition probe, an inertial filter, an analyzer, and a diluter assembly, wherein:

the gas sample acquisition probe is configured to initiate transport of a gas sample from the flue gas to the inertial filter;

the inertial filter comprises a porous filter element that removes particulate material from the gas sample and outputs a filtered gas sample;

the analyzer measures the amount of gaseous mercury present in the filtered gas sample;

the inertial filter comprises metal surfaces that are coated with a protective coating that reduces chemical reactivity of the metal surfaces to gaseous mercury;

the coated filter surfaces are positioned to contact a gas sample flowing through the filter;

the diluter assembly is coupled to the inertial filter and configured to dilute the sample gas; and the diluter assembly comprises metal surfaces that are coated with a protective coating that reduces chemical reactivity of the metal surfaces to gaseous mercury.

12. An apparatus for measuring mercury concentration in a flue gas, the apparatus comprising a gas sample acquisition probe, an inertial filter, and an analyzer, wherein:

the gas sample acquisition probe is configured to initiate transport of a gas sample from the flue gas to the inertial filter;

the inertial filter comprises a porous filter element that removes particulate material from the gas sample and outputs a filtered gas sample;

the analyzer measures the amount of gaseous mercury present in the filtered gas sample;

the inertial filter comprises metal surfaces that are coated with a protective coating that reduces chemical reactivity of the metal surfaces to gaseous mercury;

the inertial filter comprises a plurality of individual filter particles and the protective coating is provided so as to coat each of the individual filter particles; and the coated filter surfaces are positioned to contact a gas sample flowing through the filter.

* * * * *

UNITED STATES PATENT AND TRADEMARK OFFICE
CERTIFICATE OF CORRECTION

PATENT NO.         : 7,368,289 B2
APPLICATION NO. : 10/703112
DATED                 : May 6, 2008
INVENTOR(S)        : Tom Baldwin It is certified that error appears in the above-identified patent and that said Letters Patent is hereby corrected as shown below:

Col. 8, Line 2 – ¼ should read --¼"--

Signed and Sealed this

Seventeenth Day of November, 2009

David J. Kappos
*Director of the United States Patent and Trademark Office*